(12) United States Patent
Gabriel et al.

(10) Patent No.: US 6,955,678 B2
(45) Date of Patent: Oct. 18, 2005

(54) SOFT TISSUE REPAIR TOOL

(75) Inventors: Stefan Gabriel, Mattapoisett, MA (US); Justin Dye, Mansfield, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/184,829

(22) Filed: Jun. 28, 2002

(65) Prior Publication Data

US 2004/0002709 A1   Jan. 1, 2004

(51) Int. Cl.[7] ............................................. A61B 17/56
(52) U.S. Cl. ........................................ 606/104; 606/72
(58) Field of Search ............................... 606/72, 73, 79, 606/80, 96, 104, 53, 60, 75, 102, 103, 107, 606/170, 172; 600/106, 114, 117, 585; 604/117, 604/164.01, 164.06, 164.07, 164.11, 164.12, 604/164.13, 165.01, 165.02

(56) References Cited

U.S. PATENT DOCUMENTS

| | | | |
|---|---|---|---|
| 2,242,003 A | 5/1941 | Lorenzo | |
| 2,329,398 A | 9/1943 | Duffy | |
| 2,414,882 A | 1/1947 | Longfellow | |
| 2,570,465 A | 10/1951 | Lundholm | |
| 3,013,559 A | 12/1961 | Thomas | |
| 3,036,482 A | 5/1962 | Kenworthy et al. | |
| 3,289,290 A | 12/1966 | Sandor | |
| 3,832,931 A | 9/1974 | Talan | |
| 4,341,206 A * | 7/1982 | Perrett et al. | 606/80 |
| 4,450,835 A * | 5/1984 | Asnis et al. | 606/73 |
| 4,537,185 A | 8/1985 | Stednitz | |
| 4,573,448 A * | 3/1986 | Kambin | 606/170 |
| 4,744,353 A | 5/1988 | McFarland | |
| 4,790,304 A | 12/1988 | Rosenberg | |
| 4,823,780 A | 4/1989 | Odensten et al. | |
| 4,895,148 A | 1/1990 | Bays et al. | |
| 4,899,743 A | 2/1990 | Nicholson et al. | |
| 4,950,270 A | 8/1990 | Bowman et al. | |
| 4,976,715 A | 12/1990 | Bays et al. | |
| 5,098,435 A | 3/1992 | Stednitz et al. | |
| 5,120,318 A | 6/1992 | Nallapareddy | |
| 5,129,906 A | 7/1992 | Ross et al. | |

(Continued)

FOREIGN PATENT DOCUMENTS

EP   0 556 570 A   8/1993

(Continued)

OTHER PUBLICATIONS

"Acufex introduces Suretac II with Spikes", Russel Warren, Acufex Microsurgical, Inc., Document No. 994-3, 1994, 1 page.*

(Continued)

Primary Examiner—Eduardo C. Robert
Assistant Examiner—David Comstock
(74) Attorney, Agent, or Firm—Fish & Richardson P.C.

(57) ABSTRACT

A surgical tool includes a member, a guide wire received within the member by a friction fit, and a guide wire pusher for application of a force to the guide wire to overcome the friction fit and advance the guide wire relative to the member. The member includes a guide wire retainer that provides the friction fit and allows the guide wire to be held in such a way that it is pre-assembled and secure while the tool is being introduced to a surgical site. At the same time, once a hole is drilled into bone, the guide wire retainer allows the remainder of the tool to be removed leaving the guide wire in place at the site. The guide wire pusher allows the guide wire to be impacted into the bone before drilling and limits any possibility of drilling past the end of the guide wire.

35 Claims, 6 Drawing Sheets

U.S. PATENT DOCUMENTS

| | | | |
|---|---|---|---|
| 5,152,765 A | 10/1992 | Ross et al. | |
| 5,167,665 A | 12/1992 | McKinney | |
| 5,180,388 A * | 1/1993 | DiCarlo | 606/60 |
| 5,203,784 A | 4/1993 | Ross et al. | |
| 5,203,787 A | 4/1993 | Noblitt et al. | |
| 5,246,441 A | 9/1993 | Ross et al. | |
| 5,248,231 A | 9/1993 | Denham et al. | |
| 5,261,914 A | 11/1993 | Warren | |
| 5,295,970 A * | 3/1994 | Clinton et al. | 604/168.01 |
| 5,322,513 A * | 6/1994 | Walker | 604/161 |
| 5,372,599 A * | 12/1994 | Martins | |
| 5,374,270 A * | 12/1994 | McGuire et al. | 606/80 |
| 5,400,805 A * | 3/1995 | Warren | 128/898 |
| 5,415,177 A * | 5/1995 | Zadini et al. | 600/585 |
| 5,423,823 A * | 6/1995 | Schmieding | |
| 5,441,502 A * | 8/1995 | Bartlett | |
| 5,458,604 A * | 10/1995 | Schmieding | |
| 5,466,243 A * | 11/1995 | Schmieding | |
| 5,607,432 A * | 3/1997 | Fucci | |
| 5,632,745 A * | 5/1997 | Schwartz | 606/75 |
| 5,658,289 A * | 8/1997 | Boucher et al. | 606/73 |
| 5,683,401 A * | 11/1997 | Schmieding et al. | |
| 5,730,744 A * | 3/1998 | Justin et al. | |
| 5,782,835 A * | 7/1998 | Hart et al. | |
| 5,871,504 A * | 2/1999 | Eaton et al. | 606/232 |
| 5,895,389 A * | 4/1999 | Schenk et al. | 606/96 |
| 5,895,425 A * | 4/1999 | Grafton et al. | |
| 5,928,252 A * | 7/1999 | Steadman et al. | |
| 5,976,127 A * | 11/1999 | Lax | |
| 6,197,001 B1 * | 3/2001 | Wilson et al. | 604/157 |
| 6,235,057 B1 * | 5/2001 | Roger et al. | 623/13.12 |
| 6,241,734 B1 * | 6/2001 | Scribner et al. | 606/93 |
| 6,264,661 B1 * | 7/2001 | Jerger et al. | 606/100 |
| 6,270,503 B1 * | 8/2001 | Schmieding | |
| 6,375,658 B1 * | 4/2002 | Hangody et al. | 606/80 |
| 6,402,757 B1 * | 6/2002 | Moore et al. | 606/80 |
| 6,451,023 B1 * | 9/2002 | Salazar et al. | 606/86 |
| 6,613,017 B1 * | 9/2003 | Mickley | 604/117 |
| 2001/0044633 A1 | 11/2001 | Klint | |

FOREIGN PATENT DOCUMENTS

| | | | |
|---|---|---|---|
| SU | 1097 307 | * | 6/1984 |
| SU | 940 376 A | * | 2/1985 |
| WO | WO 89/10096 | * | 11/1989 |
| WO | WO 99/12480 | * | 3/1999 |

OTHER PUBLICATIONS

Arthrex, "TissueTak™II", Arthrex Inc., Document LS0504A, 2001, 1 page.*

Arthrex, "TissueTak II Surgical Technique—Bankart or SLAP Repair", Literature provided by Arthrex of Naples, FL. with the TissueTakII product, 2001, 5 pages.*

"Surgical Technique for Suretac", Russell Warren, Smith & Nephew, Inc., Document 5M1030169C, Feb., 1999, 9 pages.

* cited by examiner

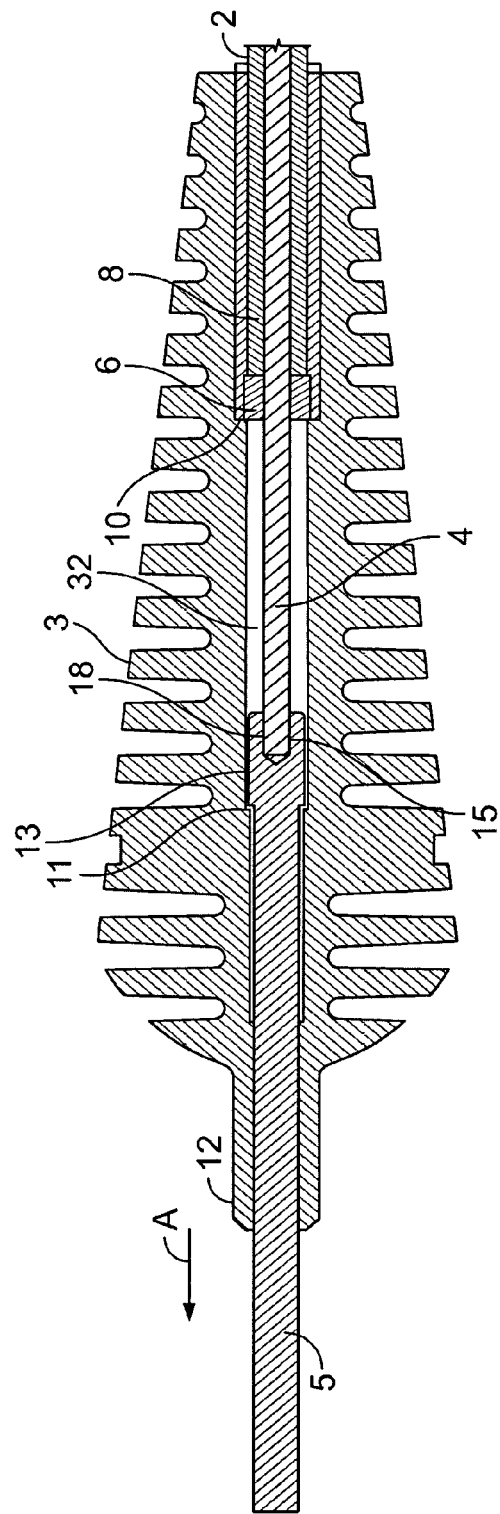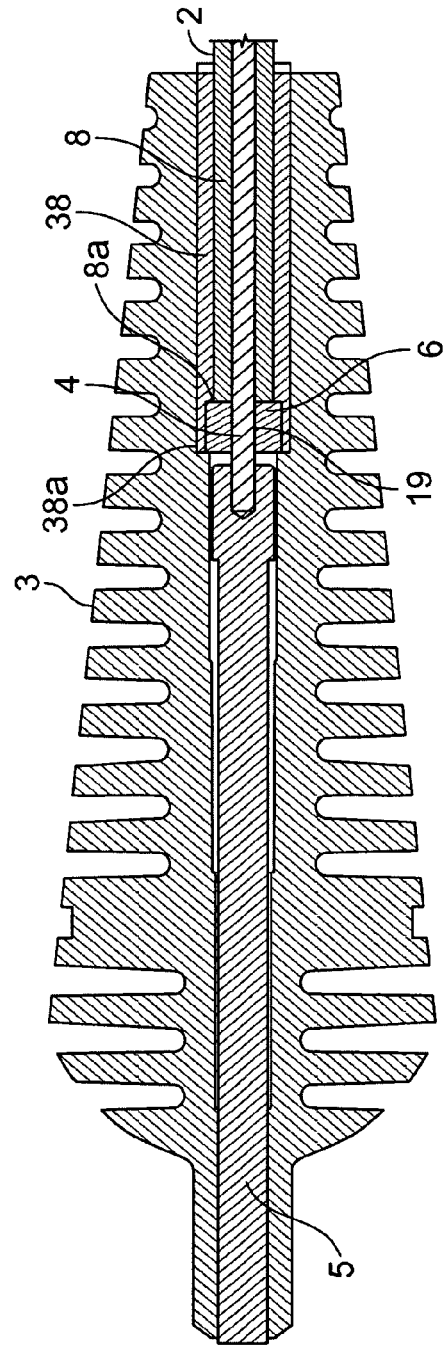
FIG. 3A
FIG. 3B

SOFT TISSUE REPAIR TOOL

This invention relates to a soft tissue repair tool, and more particularly to a tool for preparing soft tissue and bone for implantation of a tissue fastener.

BACKGROUND

When a tissue, or a portion of a tissue, is torn away from its bone attachment site, surgery to repair the detached soft tissue is often required. This is often currently done using push-in tack implants which are used to fix tendinous and ligamentous tissue to the bone at the re-attachment site. To prepare the tissue for the implant, a hole is made through the soft tissue and into the bone. The implant is subsequently passed through the soft tissue and into the bone with a portion of the implant remaining outside the hole to hold the soft tissue against the bone. Because of the need to pass the tack through the soft tissue to be re-attached, most instrument systems include a cannulated drill and guide wire. The drill and guide wire are passed through the tissue together and the drill is then used to make a hole in the bone. The guide wire is left in place in the bone hole to mark its location and provide alignment for placement of the implant. The implant is advanced over the guide wire, with a distal end of the implant passing through the soft tissue and into the bone.

SUMMARY

According to an aspect of the invention, a surgical tool includes a member, a guide wire received within the member by a friction fit, and a guide wire pusher for application of a force to the guide wire to overcome the friction fit and advance the guide wire relative to the member.

Embodiments of this aspect of the invention may include one or more of the following features.

The member includes a guide wire retainer that receives the guide wire in the friction fit. The member includes a handle and a shaft coupled to the handle. The guide wire has a sharp distal end for penetrating soft tissue and bone. The member has a drill tip for forming a hole in bone. The guide wire pusher is arranged relative to the member to limit a depth to which the member can be advanced into bone. The member defines an internal shoulder which the guide wire pusher contacts to limit relative movement between the member and the guide wire pusher. The member is configured to provide the friction fit such that the guide wire is pre-assembled and secure within the member when the member is being introduced to a surgical site, and the friction fit is overcome when the guide wire is inserted into bone and the member is retracted relative to the guide wire.

According to another aspect of the invention, a method includes advancing a surgical tool to a surgical site, the surgical tool including a member, a guide wire received in the member, and a guide wire pusher, and applying a force to the guide wire pusher to advance the guide wire into bone moving the guide wire relative to the member to overcome a friction fit securing the guide wire to the member.

Embodiments of this aspect of the invention may include one or more of the following features.

The method includes advancing the member relative to the guide wire to form a hole in the bone for receiving an implant. The advancement of the member relative to the guide wire is limited by interaction of the guide wire pusher with the member. The method includes withdrawing the member from the surgical site while maintaining the guide wire at the surgical site by overcoming the friction fit, and advancing an implant over the guide wire and into the bone hole.

The guide wire retainer provides the friction fit and allows the guide wire to be held in such a way that it is pre-assembled and secure while the tool is being introduced to a surgical site. At the same time, once a hole is drilled into bone, the guide wire retainer allows the remainder of the tool to be removed leaving the guide wire in place at the site. The guide wire pusher allows the guide wire to be impacted into the bone before drilling and limits any possibility of drilling past the end of the guide wire.

Advantages of the invention may include one or more of the following features.

A soft tissue repair tool for bone preparation and implant deployment is easy to use, is presented pre-assembled in a single-case, pre-sterilized format, does not require separate assembly and dis-assembly steps, controls the relative position between the guide wire and shaft both before, during, and after drilling, requires only two instrument components, a drill tool and an inserter, to deploy an implant, and can be used arthroscopically or in an open or mini-open procedure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A is a cross-sectional view of a handle region of the drill tool;

FIG. 3B is a cross-sectional view of the handle region showing a guide wire pusher advanced distally;

DETAILED DESCRIPTION

Figure 1:
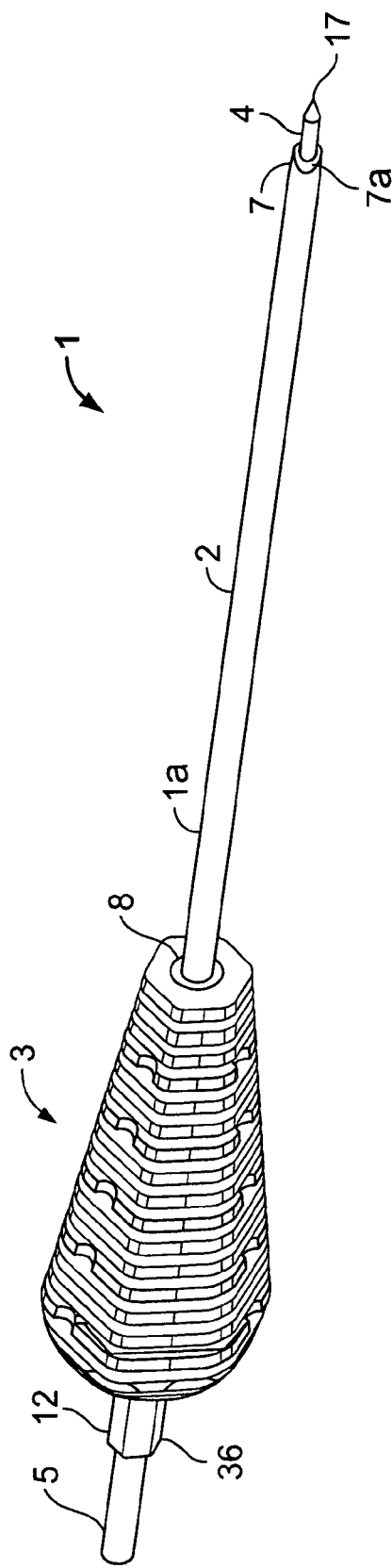
FIG. 1 is a perspective view of a drill tool according to the invention.
Figure 2:
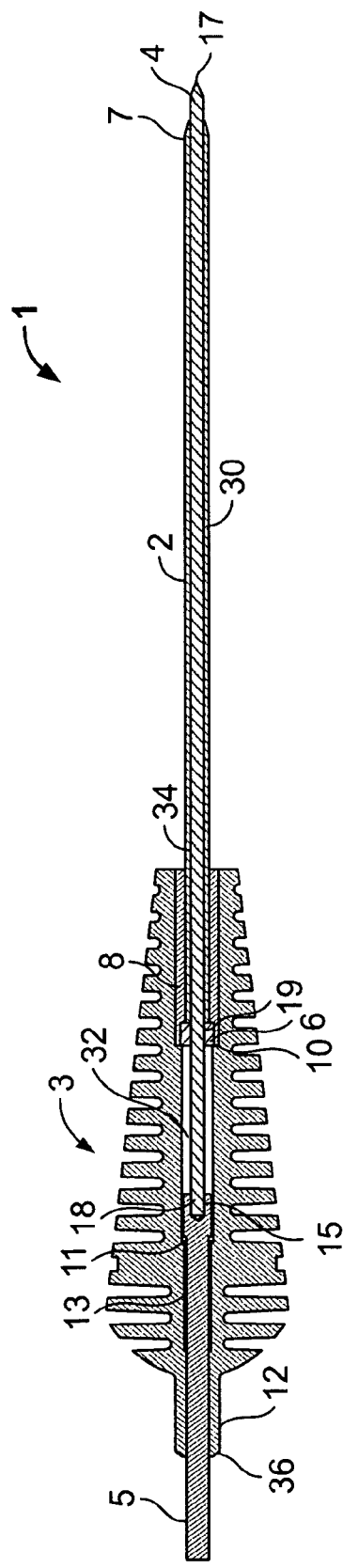
FIG. 2 is a cross-sectional view of the drill tool.

Referring to FIGS. 1 and 2, a drill tool 1 for preparing tissue to receive an implant includes an elongate member 1a having a shaft 2 and a handle 3 attached to a proximal region 8 of shaft 2, e.g., by pressing, gluing or welding. Shaft 2 defines a lumen 30, and handle 3 defines a lumen 32. Lumens 30, 32 are aligned and create a through passage 34 from a proximal end 36 of handle 3 to a distal end 7 of shaft 2. Tool 1 includes a guide wire 4 received within lumen 30 of shaft 2 and axially translatable relative to shaft 2, a guide wire pusher 5 received within lumen 32 of handle 3 and axially translatable relative to handle 3, and a guide wire retainer 6 received within proximal region 8 of shaft 2 that frictionally engages guide wire 4, for purposes described below. Guide wire 4 has a distal, sharp point 17 for penetrating soft tissue and bone, and shaft distal end 7 is formed to a sharp drilling tip 7a for forming a hole in bone. Handle 3 has a proximal hex feature 12 that allows releasable attachment of tool 1 to a power drilling tool (not shown).

Referring to FIG. 3A, handle 3 has a first internal shoulder 10 extending into lumen 32, against which shaft 2 and guide wire retainer 6 are held, and a second internal shoulder 11 extending into lumen 32, which limits the proximal translation of the guide wire pusher 5 (arrow, A) by engagement of an enlarged, distal end 13 of guide wire pusher 5 with shoulder 11. Guide wire pusher distal end 13 defines an axially oriented blind hole 15 opening distally for removably receiving a proximal end 18 of guide wire 4. As shown in FIG. 3B, guide wire pusher 5 is used to distally advance guide wire 4 relative to shaft 2.

Figure 4:
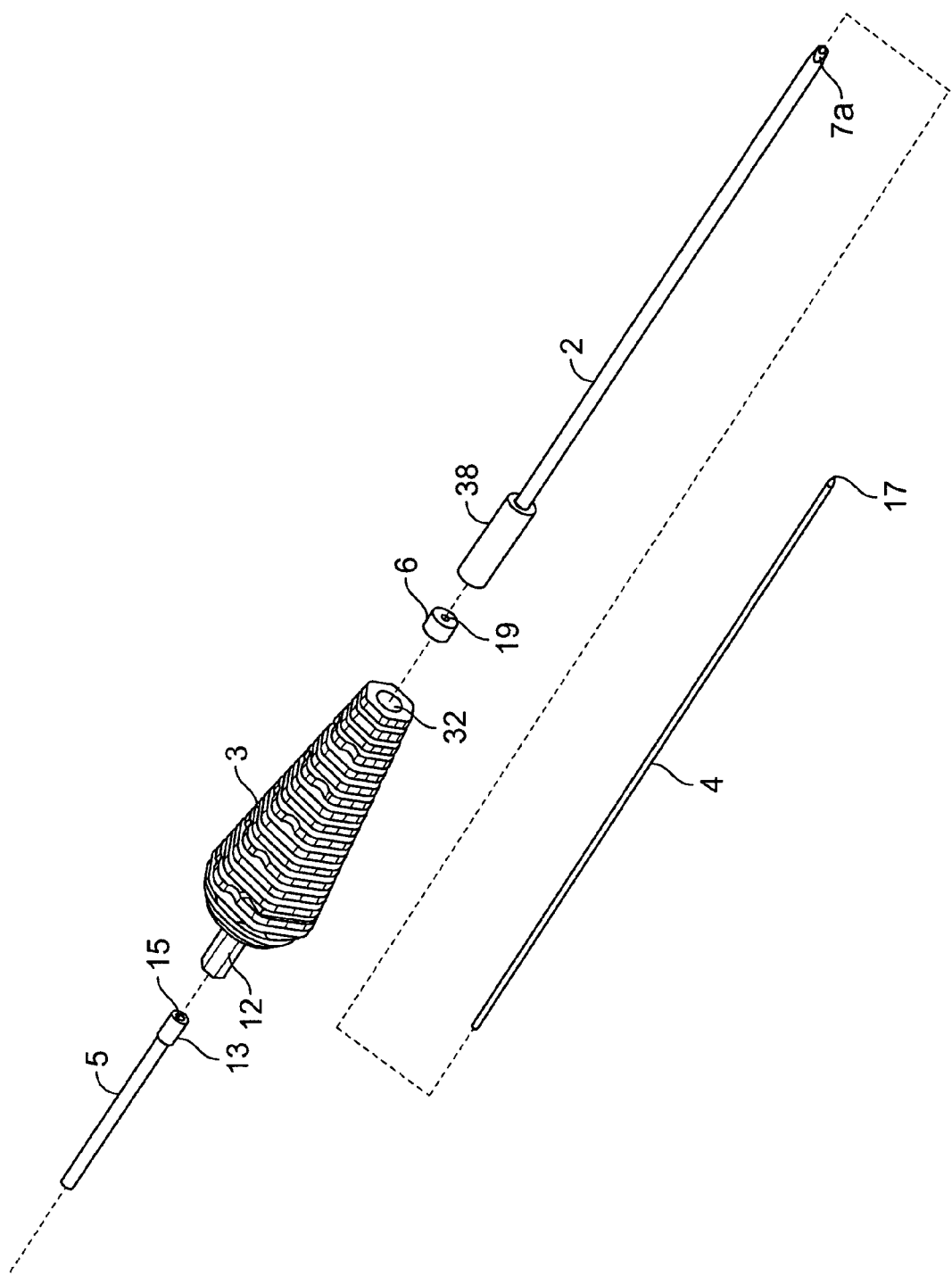
FIG. 4 is an exploded view of the drill tool.

Referring also to FIG. 4, surrounding proximal region 8 of shaft 2 is an outer cylindrical member 38 having an enlarged inner diameter region 38a for receiving guide wire retainer 6. Shaft 2 has a proximal end 8a that abuts against guide wire retainer 6. Guide wire retainer 6 defines a channel 19 through which guide wire 4 passes. There is a frictional fit between guide wire 4 and guide wire retainer 6 such that guide wire 4 is retained within tool 1 until guide wire 4 is fixed in the bone and tool 1 is removed from the bone, as described below.

Figure 5:
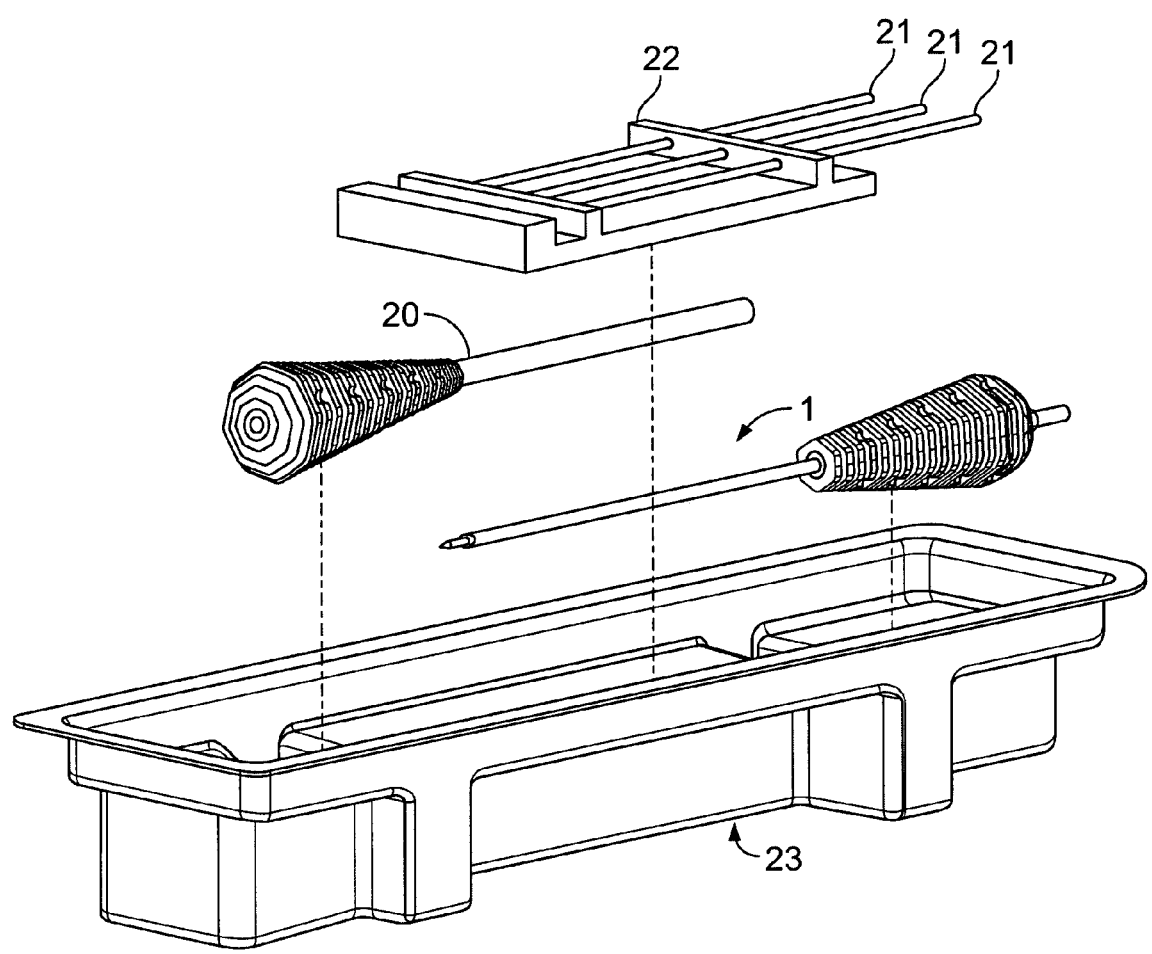
FIG. 5 is an exploded view of a packaged tissue preparation and implant deployment assembly.

Referring to FIG. 5, tool 1 is preferably packaged sterile with an implant inserter 20 and extra guide wires 21 in a foam carrier 22 (in case the guide wire 4 supplied in tool 1 is damaged during a procedure before all implants for that procedure are implanted) in a disposable tray 23. The components of tool 1 are preferably manufactured by polymer molding processes and machining and pressed assembled, though other methods using biocompatible metal (s) and polymer(s) can be used.

Figure 6A:
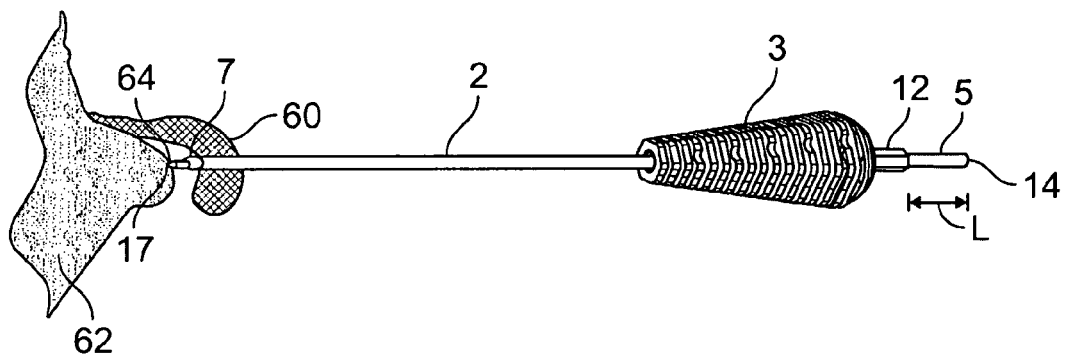
FIGS. 6A–6E show the drill tool in use.
Figure 6B:
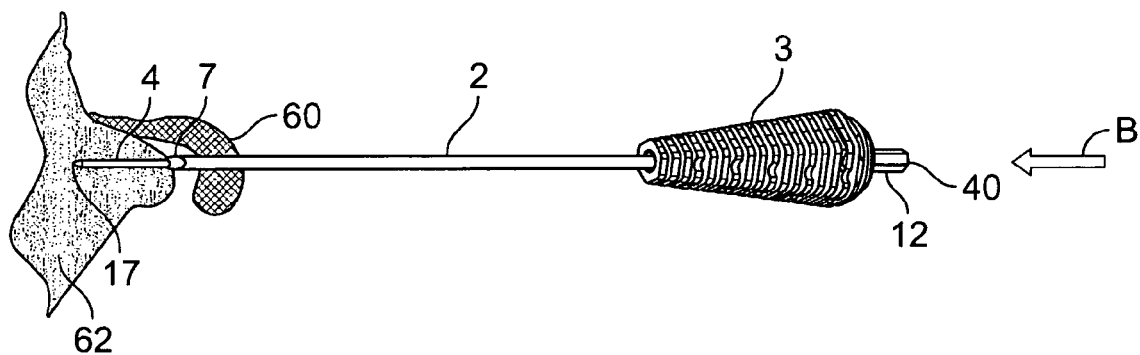

Referring to FIG. 6A, in use, with guide wire 4 positioned relative to shaft 2 as shown in FIG. 1, i.e., with guide wire pusher 5 against internal shoulder 11, the operator passes distal point 17 of guide wire 4 and distal end 7 of shaft 2 through soft tissue 60 and against bone 62 at the reattachment site 64 on the bone. Referring also to FIG. 6B, the operator than impacts guide wire pusher 5 (arrow, B) with, e.g., a hammer, overcoming the friction fit between guide wire 4 and guide wire retainer 6 to advance guide wire 4 relative to shaft 2, until a proximal end 14 of guide wire pusher 5 is flush with a proximal end 40 of handle hex feature 12. This action lodges the distal end of guide wire 4 in bone 62 a distance equal to the length, l, of guide wire pusher 5 that extends from proximal end 40 when guide wire pusher 5 is against internal shoulder 11.

Figure 6C:
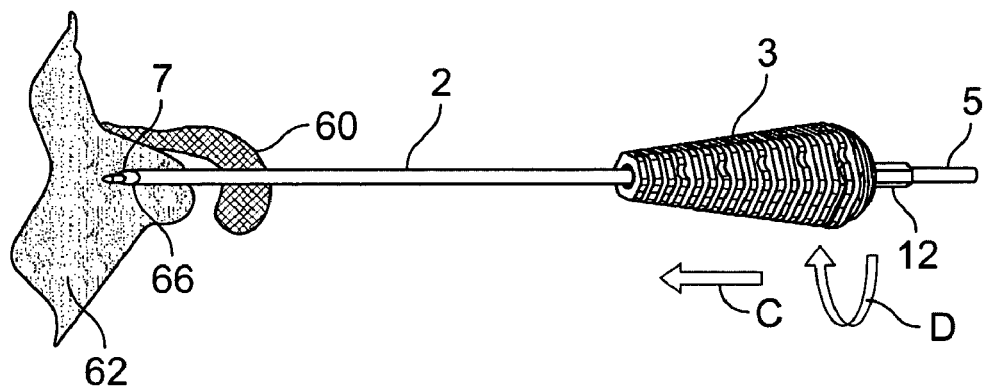

Referring to FIG. 6C, the operator then advances (arrow, C) and rotates (arrow, D) handle 3 and shaft 2, either by hand or with a power drill coupled to hex feature 12, to form a hole 66 in bone 62 greater than or equal to the length of the portion of the implant to be deployed within the bone. This can be aided by length markings (not shown) on shaft 2. The advancement of shaft 2 moves shaft 2 relative to guide wire 4 such that guide wire pusher 5 again protrudes from proximal end 40 of handle 3, and guide wire 4 is retained within shaft 2 by the friction fit with retainer 6. The operator then gives guide wire pusher 5 a few taps to dislodge any debris which may have become lodged in lumen 30 of shaft 2.

Figure 6D:
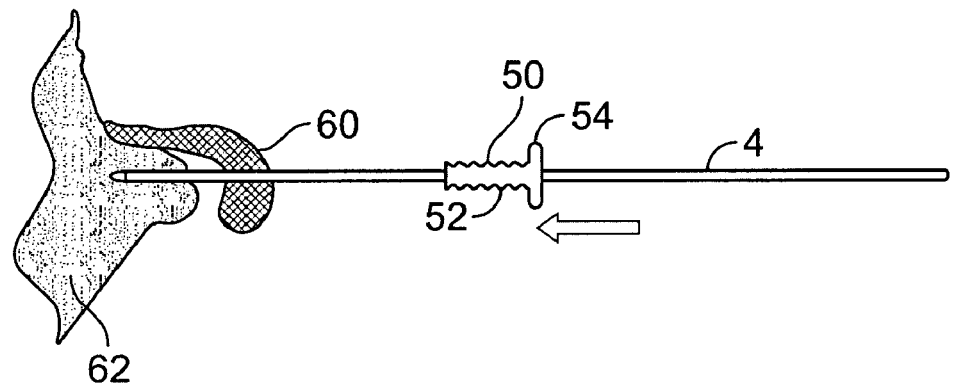

Referring to FIG. 6D, the operator then removes shaft 2, handle 3, pusher 5, and retainer 6 from the patient. The friction fit is selected such that the force to overcome the lodgment of guide wire 4 within the bone is greater than the force to overcome the friction fit, such that guide wire 4 remains in place in the bone when the remainder of tool 1 is removed. The operator then places an implant 50, such as a Suretac® tissue tack available from Smith & Nephew, Inc., Andover, Mass., catalog number 014567, on guide wire 4, and uses inserter 20 (FIG. 5) to push implant 50 into the bone. Impaction is usually necessary to aid in this step. The operator then removes guide wire 4 from the bone.

Figure 6E:
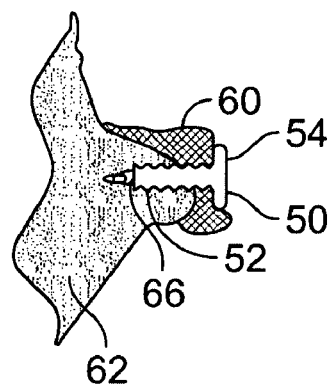

Referring to FIG. 6E, implant 50 is preferably a tack with a shaft 52 and a head 54. Shaft 52 is implanted into hole 66 drilled in the bone, and head 554 captures and holds down the soft tissue 60 being re-attached to bone 62.

A number of embodiments of the invention have been described. Nevertheless, it will be understood that various modifications may be made without departing from the spirit and scope of the invention. Accordingly, other embodiments are within the scope of the following claims.

What is claimed is:

1. A surgical tool, comprising:
   a member,
   a guide wire received within the member by a friction fit, and
   a guide wire pusher for application of a force to the guide wire to overcome the friction fit and advance the guide into tissue wire relative to the member, wherein the guide wire pusher is arranged to advance relative to the member a length about equal to the advancement of the guide wire.

2. The surgical tool of claim 1 wherein the member includes a guide wire retainer that receives the guide wire in the friction fit.

3. The surgical tool of claim 1 wherein the member includes a handle and a shaft coupled to the handle.

4. The surgical tool of claim 1 wherein the guide wire has a sharp distal end for penetrating soft tissue and bone.

5. The surgical tool of claim 1 wherein the member has a drill tip for forming a hole in bone.

6. The surgical tool of claim 1 wherein the member defines an internal shoulder which the guide wire pusher contacts to limit relative movement between the member and the guide wire pusher.

7. The surgical tool of claim 1 wherein the member is configured to provide the friction fit such that the guide wire is pre-assembled and secure within the member when the member is being introduced to a surgical site, and the friction fit is overcome when the guide wire is inserted into bone and the member is retracted relative to the guide wire.

8. A surgical tool, comprising:
   a member having a proximal end,
   a guide wire received within the member by a friction fit, and
   a guide wire pusher received within the member and extending from the proximal end of the member for application of a force to the guide wire to overcome the friction fit and advance the guide wire relative to the member.

9. The surgical tool of claim 8 wherein the member includes a guide wire retainer that receives the guide wire in the friction fit.

10. The surgical tool of claim 8 wherein the member includes a handle and a shaft coupled to the handle.

11. The surgical tool of claim 8 wherein the guide wire has a sharp distal end for penetrating soft tissue and bone.

12. The surgical tool of claim 8 wherein the member has a drill tip for forming a hole in bone.

13. The method of claim 12 wherein the advancement of the member is limited by interaction of the guide wire pusher with the member.

14. The method of claim 12 further comprising withdrawing the member from the surgical site while maintaining the guide wire at the surgical site by overcoming the friction fit.

15. The method of claim 12 further comprising advancing an implant over the guide wire and into the hole.

16. The surgical tool of claim 8 wherein the member defines an internal shoulder which the guide wire pusher contacts to limit relative movement between the member and the guide wire pusher.

17. The surgical tool of claim 8 wherein the member is configured to provide the friction fit such that the guide wire is pre-assembled and secure within the member when the member is being introduced to a surgical site, and the friction fit is overcome when the guide wire is inserted into bone and the member is retracted relative to the guide wire.

18. A surgical tool, comprising:
a member having a drill tip,
a guide wire received within the member by a friction fit, and
a guide wire pusher for application of a force to the guide wire to overcome the friction fit and advance the guide wire relative to the member and into tissue.

19. The surgical tool of claim 18, wherein the member is advanceable relative to the guide wire and the guide wire pusher is arranged relative to the member to substantially set a predetermined distance the member is advanced relative to the guide wire.

20. The surgical tool of claim 18, wherein the guide wire pusher is arranged relative to the member to substantially set a predetermined distance the guide wire is advanced into the tissue.

21. A method comprising:
advancing a surgical tool to a surgical site, the surgical tool including a member, a guide wire received in the member, and a guide wire pusher,
applying a force to the guide wire pusher to advance the guide wire into tissue by moving the guide wire relative to the member to overcome a friction fit securing the guide wire to the member,
wherein the guide wire pusher is arranged to advance relative to the member a length about equal to the advancement of the guide wire.

22. The method of claim 21 wherein the tissue comprises bone.

23. The method of claim 22 further comprising advancing the member relative to the guide wire to form a hole in the bone for receiving an implant.

24. The method of claim 23 wherein the advancement of the member is limited by interaction of the guide wire pusher with the member.

25. The method of claim 23 further comprising withdrawing the member from the surgical site while maintaining the guide wire at the surgical site by overcoming the friction fit.

26. The method of claim 25 further comprising advancing an implant over the guide wire and into the bone hole.

27. A method comprising:
advancing a surgical tool to a surgical site, the surgical tool including a member, a guide wire received in the member, and a guide wire pusher;
applying a force to the guide wire pusher to advance the guide wire into bone moving the guide wire relative to the member to overcome a friction fit securing the guide wire to the member; and
advancing the member into the bone.

28. The method of claim 27 wherein the advancement of the member relative to the guide wire is limited.

29. The method of claim 28, wherein the guide wire pusher is arranged relative to the member to substantially set a predetermined distance the member is advance relative to the guide wire.

30. The method of claim 27, wherein the guide wire pusher is arranged relative to the member to substantially set a predetermined distance the guide wire is advance into the bone.

31. A method comprising:
advancing a surgical tool to a surgical site, the surgical tool including a member, a guide wire received in the member, and a guide wire pusher;
applying a force to the guide wire pusher to advance the guide wire into bone moving the guide wire relative to the member to overcome a friction fit securing the guide wire to the member; and
advancing the member relative to the guide wire to form a hole in the bone for receiving an implant.

32. The method of claim 31 wherein the advancement of the member relative to the guide wire is limited.

33. The method of claim 32 wherein the advancement of the member is limited by interaction of the guide wire pusher with the member.

34. The method of claim 31 further comprising withdrawing the member from the surgical site while maintaining the guide wire at the surgical site by overcoming the friction fit.

35. The method of claim 34 further comprising advancing an implant over the guide wire and into the bone hole.

* * * * *

UNITED STATES PATENT AND TRADEMARK OFFICE
CERTIFICATE OF CORRECTION

PATENT NO. : 6,955,678 B2 Page 1 of 1
APPLICATION NO. : 10/184829
DATED : October 18, 2005
INVENTOR(S) : Stefan Gabriel and Justin Dye It is certified that error appears in the above-identified patent and that said Letters Patent is hereby corrected as shown below:

Column 6, claim 29, line 16, "advance" should be --advanced--.
Column 6, claim 30, line 20, "advance" should be --advanced--.

Signed and Sealed this

Twenty-first Day of August, 2007

JON W. DUDAS
*Director of the United States Patent and Trademark Office*